(12) United States Patent
Uematsu et al.

(10) Patent No.: US 7,829,327 B2
(45) Date of Patent: Nov. 9, 2010

(54) OPTICAL WAVEGUIDE TYPE ANTIBODY CHIP AND METHOD OF MEASURING ANTIGEN CONCENTRATION

(75) Inventors: Ikuo Uematsu, Yokohama (JP);
Masatoshi Sakai, Yokohama (JP);
Shingo Kasai, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 426 days.

(21) Appl. No.: 12/047,670

(22) Filed: Mar. 13, 2008

(65) Prior Publication Data
US 2008/0227126 A1    Sep. 18, 2008

(30) Foreign Application Priority Data
Mar. 14, 2007  (JP)  ............. 2007-065374

(51) Int. Cl.
*G01N 33/551*  (2006.01)
*G01N 33/552*  (2006.01)

(52) U.S. Cl. ............ 435/287.2; 385/12; 385/129; 385/130; 422/58; 422/82.05; 422/82.11; 435/288.7; 435/808; 436/164; 436/165; 436/524; 436/527; 436/805; 436/807

(58) Field of Classification Search .............. None
See application file for complete search history.

(56) References Cited

U.S. PATENT DOCUMENTS
6,469,785 B1 * 10/2002 Duveneck et al. ........... 356/244

FOREIGN PATENT DOCUMENTS
JP          3-7270          2/1991

* cited by examiner

*Primary Examiner*—Christopher L Chin
(74) *Attorney, Agent, or Firm*—Oblon, Spivak, McClelland, Maier & Neustadt, L.L.P.

(57) ABSTRACT

An optical waveguide type antibody chip includes a transparent substrate, an incident-side optical element and an emitting-side optical element placed at a distance from each other on a primary face of the substrate, a water repellent resin film formed on the primary face of the substrate including an optical waveguide layer formed between the optical elements, the water repellent resin film includes a reaction hole having exposed the optical waveguide layer on its bottom and a frame-shaped trench surrounding the reaction hole, a rectangular frame-shaped cell wall which is fixed in the trench of the water repellent resin film and which forms a cell capable of infusion and discharge of a specimen solution together with the reaction hole, and an antibody immobilization layer formed on the bottom of the reaction hole, the surface of the antibody immobilization layer being masked with at least a buffer agent and a salt.

12 Claims, 5 Drawing Sheets

Laser beam

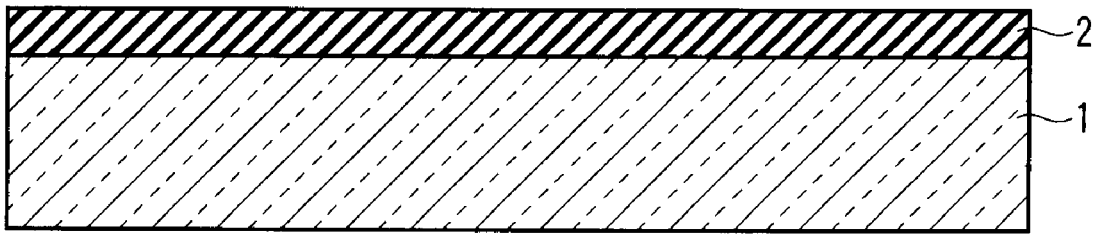
F I G. 3A
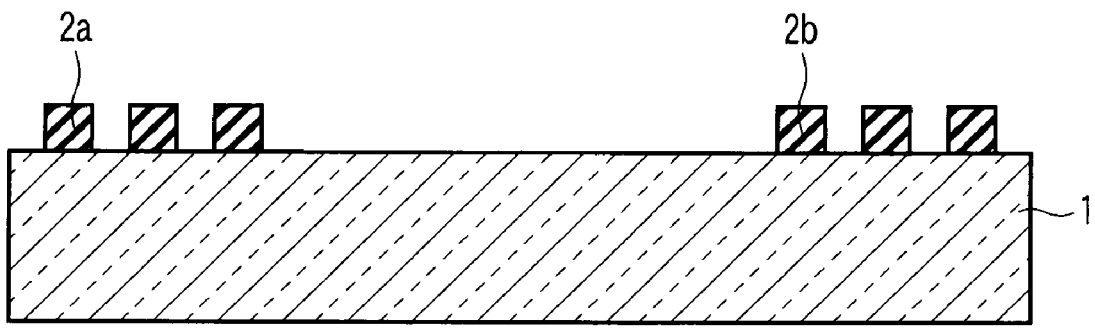
F I G. 3B
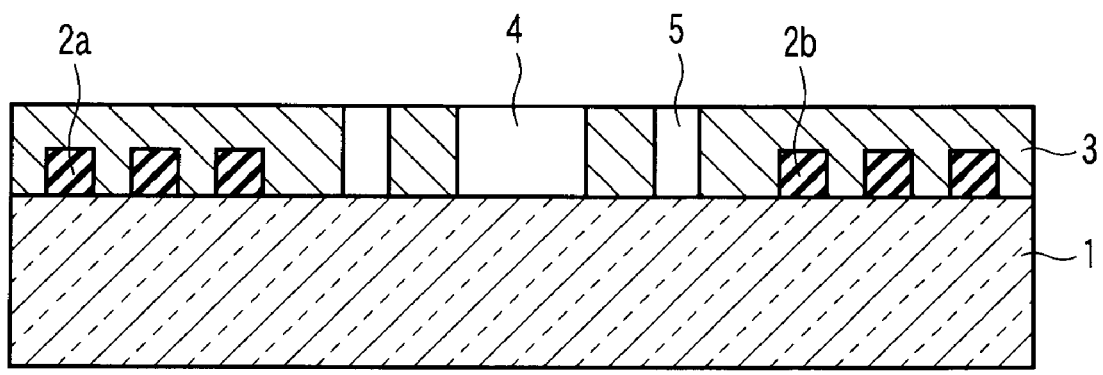
F I G. 3C

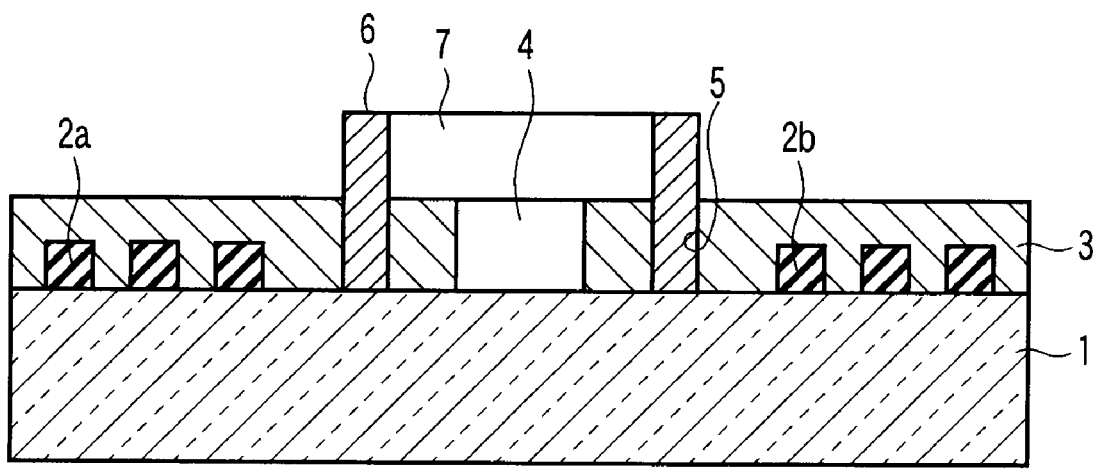
F I G. 3D
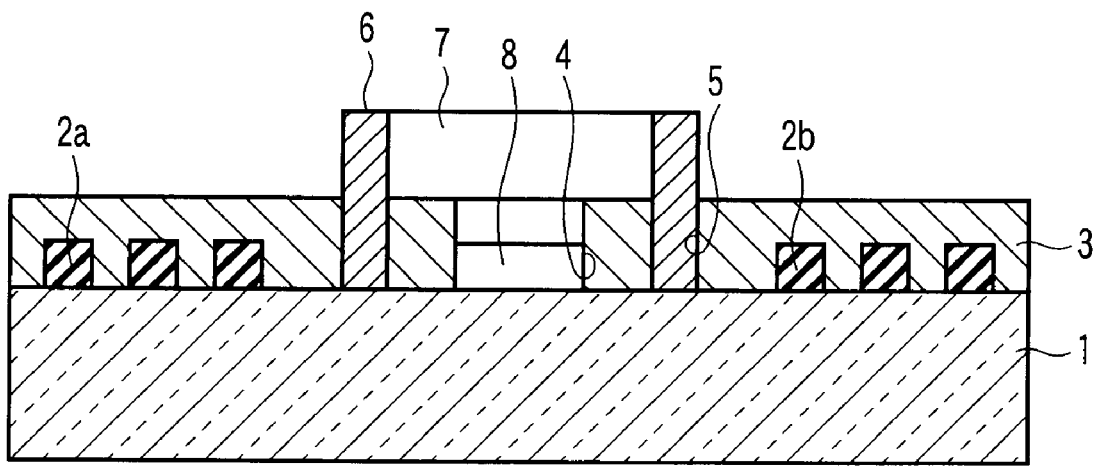
F I G. 3E

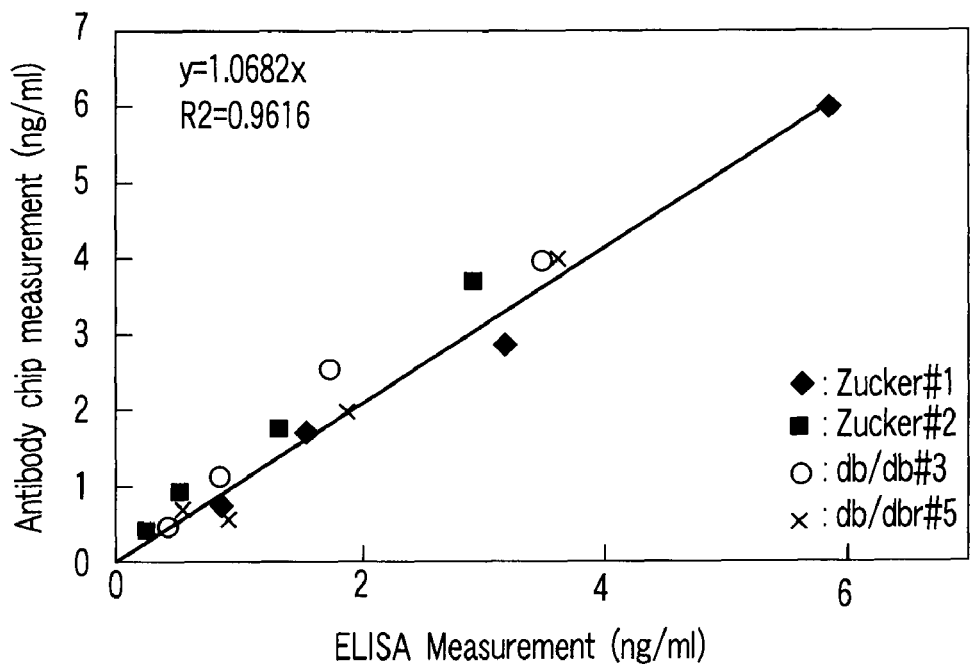
F I G. 4
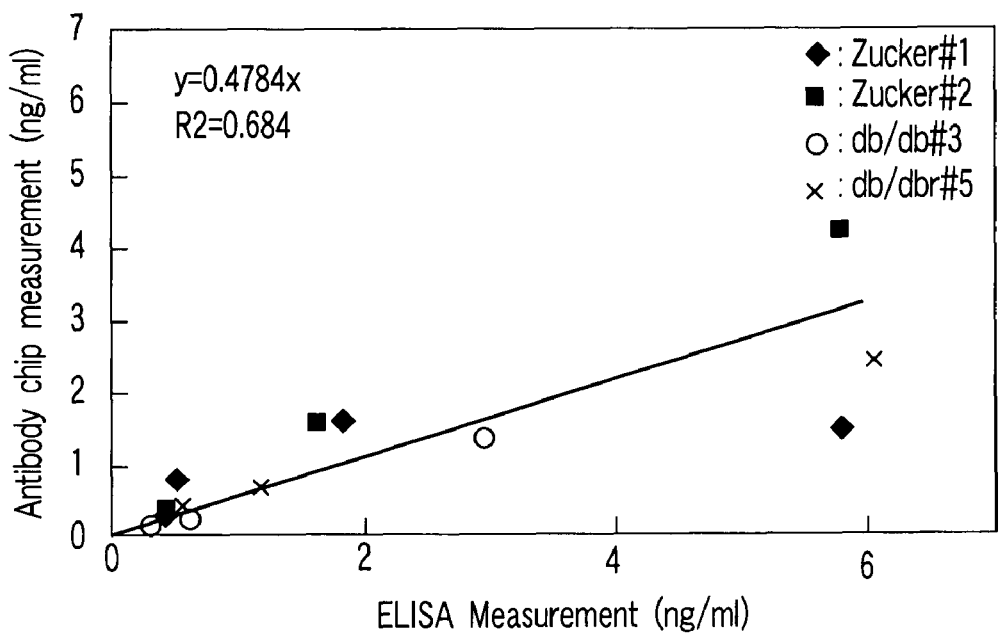
F I G. 5

OPTICAL WAVEGUIDE TYPE ANTIBODY CHIP AND METHOD OF MEASURING ANTIGEN CONCENTRATION

CROSS-REFERENCE TO RELATED APPLICATIONS

This application is based upon and claims the benefit of priority from prior Japanese Patent Application No. 2007-065374, filed Mar. 14, 2007, the entire contents of which are incorporated herein by reference.

BACKGROUND OF THE INVENTION

1. Field of the Invention

The present invention relates to an optical waveguide type antibody chip and a method of measuring an antigen concentration using the chip.

2. Description of the Related Art

Conventionally, an enzyme-linked immunosorbent assay method (hereinafter, referred to as the ELISA method) has been put to practical use in the field of clinical laboratory testing, etc. as a method of measuring trace components by making use of a specific antigen-antibody reaction.

The ELISA method uses a resin plate having arranged therein 96 dents (wells), which is usually called a microplate. For example, in the sandwich ELISA method, a primary antibody is immobilized in each well according to its purpose. First, a specimen solution is poured into wells and an antibody immobilized on the plate is allowed to react with a measuring target substance in the specimen solution (hereinafter, referred to as primary reaction). Subsequently, the unreacted substances in the specimen solution are removed by cleaning. Thereafter, a solution of a secondary antibody marked with an enzyme is poured into wells and the secondary antibody is allowed to specifically react with the measuring target substance having reacted with the primary antibody (hereinafter, referred to as secondary reaction). The unreacted substances in the secondary specimen solution are removed by cleaning. A color reagent solution is poured into a well and subjected to an enzyme reaction to make the enzyme reaction product exhibit color. The absorbance is measured from the transmission light quantity of the well using a microplate reader. This absorbance is collated with a calibration curve prepared in advance to obtain the concentration of the measuring target substance.

For example, in order to form a diagnosis or pathosis of diabetes mellitus, the insulin concentration in blood is measured. Insulin is known to be a hormone secreted from the β cells of the pancreas and have a blood glucose lowering action. When the level of insulin is determined by the ELISA method, a specimen solution is poured into wells in a microplate on which an anti-insulin antibody is immobilized, and the anti-insulin antibody is caused to react with the insulin to obtain the insulin concentration according to the procedure described above.

The ELISA method using a microplate requires several dozen μL to about 100 μL of a specimen as a measuring specimen. At the minimum, 5 μL or more of a specimen is needed. Below this amount, the measuring sensitivity is too low, at only several thousands pg/mL.

As a different method, a sensor plate making use of an antigen-antibody reaction is disclosed in Jpn. Pat. Appln. KOKAI Publication No. 8-285851. This optical waveguide type sensor plate includes a glass plate, an optical waveguide layer constituted by a silicon nitride film formed on the substrate, incident-side and emitting-side gratings (refraction gratings) formed on both the ends of the optical waveguide layer, and an antibody immobilization layer formed on the optical waveguide layer. A prism can be used instead of a grating.

In the sensor plate having such a construction, the contact of a specimen solution containing an antigen on the antibody immobilization layer leads to an antigen-antibody reaction. When an antibody solution marked with a fluorescent dye is added to the antibody immobilization layer, an immune complex constituted by an antibody/antigen/fluorescent dye marked antibody is formed on the substrate. In this state, a laser beam is directed into the optical waveguide through the incident-side grating to generate an evanescent wave in the course of allowing the beam to propagate through the optical waveguide. The evanescent wave excites the fluorescent dye in the antibody immobilization layer on the optical waveguide layer and radiates fluorescence. The amount of fluorescence discharged from the fluorescent dye is detected by a light receiving element facing the antibody immobilization layer, whereby the antigen concentration in the specimen solution is measured.

Such evanescent wave is an electromagnetic wave generated only in the vicinity of the interface between an optical waveguide and an external layer when light is totally reflected at the interface. The known measuring methods using an evanescent wave also include, in addition to a method of marking with a fluorescent dye, a method of detecting changes in physical quantities of reflection light arising from the absorption of an evanescent wave in a pigment marked substance in a specimen (e.g., a secondary antibody marked with a pigment) (see Jpn. Pat. Appln. KOKOKU Publication No. 3-7270).

However, when the above sensor plate is used to measure the amount of insulin in blood plasma of, for example, a model rat (e.g., Zucker), the detection value is considerably lower than the actual value. In other words, it poses the problem of low detection reproducibility.

BRIEF SUMMARY OF THE INVENTION

According to a first aspect of the present invention, there is provided an optical waveguide type antibody chip, comprising:

a transparent substrate;

an incident-side optical element and an emitting-side optical element placed at a distance from each other on a primary face of the substrate;

a water repellent resin film formed on the primary face of the substrate including an optical waveguide layer formed between the optical elements, the water repellent resin film comprising a reaction hole having exposed the optical waveguide layer on its bottom and a frame-shaped trench surrounding the reaction hole;

a rectangular frame-shaped cell wall which is fixed in the trench of the water repellent resin film and which forms a cell capable of infusion and discharge of a specimen solution together with the reaction hole; and an antibody immobilization layer formed on the bottom of the reaction hole, the surface of the antibody immobilization layer being masked with a masking composition comprising at least a buffer agent and a salt.

According to a second aspect of the present invention, there is provided a method of measuring an antigen concentration, comprising:

providing an optical waveguide type antibody chip comprising:

(a) a transparent substrate;

(b) an incident-side optical element and an emitting-side optical element placed at a distance from each other on a primary face of the substrate;

(c) a water repellent resin film formed on the primary face of the substrate including an optical waveguide layer formed between the optical elements, the water repellent resin film comprising a reaction hole having exposed the optical waveguide layer on its bottom and a frame-shaped trench surrounding the reaction hole;

(d) a rectangular frame-shaped cell wall which is fixed in the trench of the water repellent resin film and which forms a cell capable of infusion and discharge of a specimen solution together with the reaction hole; and (e) an antibody immobilization layer formed on the bottom of the reaction hole, the surface of the antibody immobilization layer being masked with a masking composition comprising at least a buffer agent and a salt;

adding dropwise a specimen solution containing an antigen onto the antibody immobilization layer within the cell to form a primary antibody-antigen complex;

adding dropwise a secondary antibody marked with an enzyme onto the antibody immobilization layer to form a primary antibody-antigen-secondary antibody complex;

adding dropwise a color reagent onto the antibody immobilization layer to allow the color reagent to react with the enzyme of the secondary antibody, thereby forming an enzyme reactant exhibited color;

causing light to be incident on an optical waveguide layer of the substrate from the incident-side optical element with respect to the substrate before and after the dropwise addition of the color reagent;

receiving the light emitted from the emitting-side optical element through the optical waveguide layer to measure light intensities before and after the dropwise addition of the color reagent; and calculating the antigen concentration in the specimen solution on the basis of the difference in the light intensities.

BRIEF DESCRIPTION OF THE SEVERAL VIEWS OF THE DRAWING

FIGS. 3A, 3B, 3C, 3D and 3E are sectional views showing a process of producing an optical waveguide type antibody chip according to the embodiment of the invention;

FIG. 4 is a graph showing a relation between measurements (y) of insulin concentrations of various rats and mice, calculated from Examples 1 to 4, and measurements (x) of insulin concentrations of various rats and mice, calculated by the ELISA method;

FIG. 5 is a graph showing a relation between measurements (y) of insulin concentrations of various rats and mice, calculated from Comparative Examples 1 to 4, and measurements (x) of insulin concentrations of various rats and mice, calculated by the ELISA method.

DETAILED DESCRIPTION OF THE INVENTION

An optical waveguide type antibody chip and a method of measuring an antigen concentration according to an embodiment of the present invention will be described in detail with reference to the drawings hereinafter.

Figure 1:
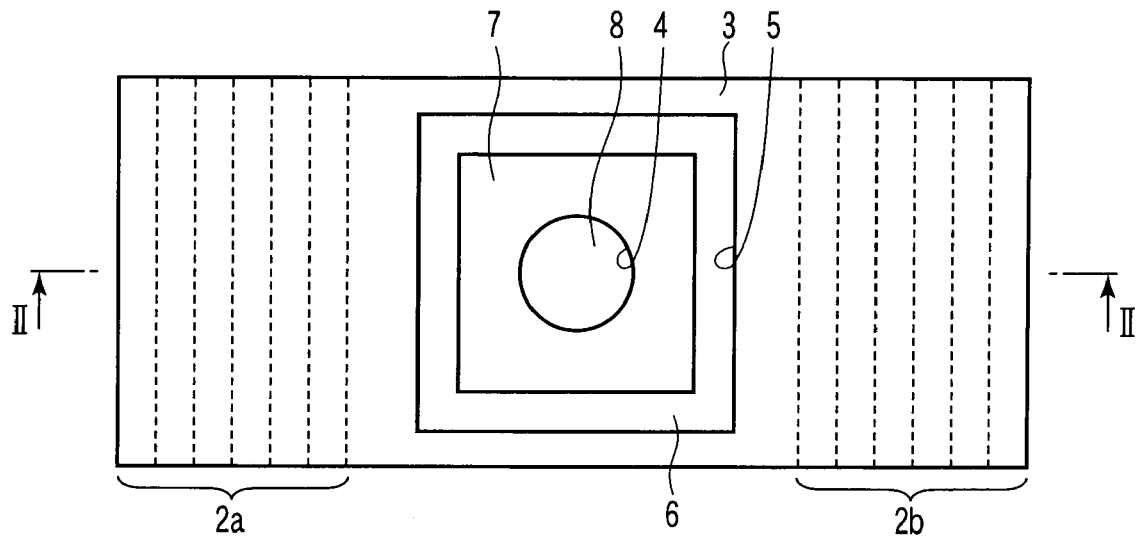
FIG. 1 is a plan view showing one example of an optical waveguide type antibody chip according to an embodiment of the present invention.
Figure 2:
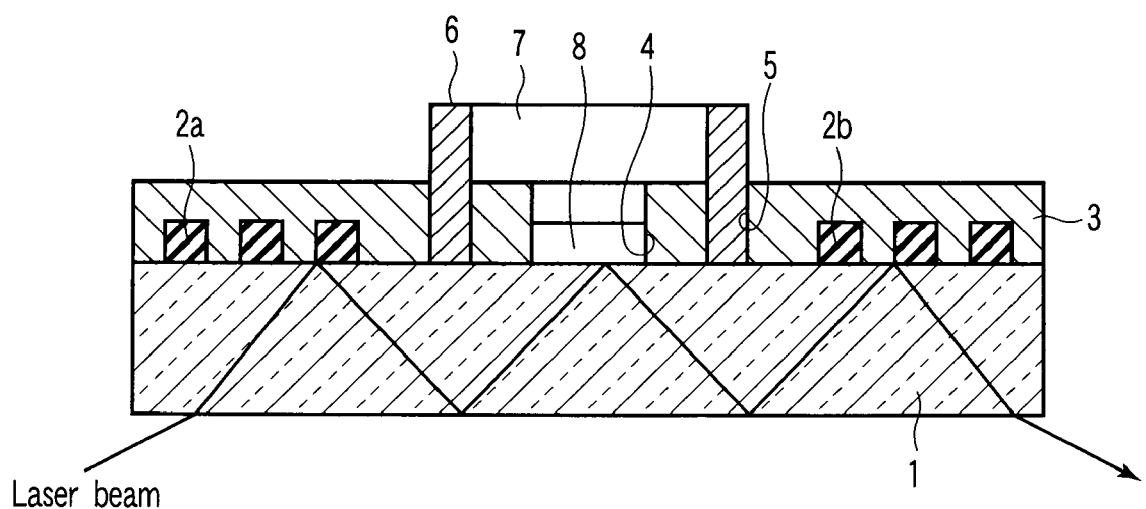
FIG. 2 is a sectional view taken along the line II-II of FIG. 1.

FIG. 1 is a plan view showing an optical waveguide type antibody chip according to the embodiment, and FIG. 2 is a sectional view taken along the line II-II of FIG. 1.

On both the ends of a primary face of a transparent substrate 1 constituted by, for example, borosilicate glass, there are arranged an incident-side grating 2a, which is an incident-side optical element, and an emitting-side grating 2b, which is an emitting-side optical element. The gratings 2a, 2b are arranged on both the ends of the primary face of the substrate 1 to form an optical waveguide layer in the substrate 1 therebetween. A water repellent resin film 3 is coated on the entire primary face of the substrate 1 including the optical waveguide layer formed in the substrate 1 between the gratings 2a, 2b. In the water repellent resin film 3, a circular reaction hole 4 having the optical waveguide layer exposed on its bottom is formed. In addition, for example, a rectangular frame-shaped trench 5 is formed in the water repellent resin film 3. The trench 5 surrounds the reaction hole 4 and exposes the optical waveguide layer on its bottom. A rectangular frame-shaped cell wall 6 is fixed in the trench 5 of the water repellent resin film 3. The rectangular frame-shaped cell wall 6 together with the reaction hole 4 forms a cell 7 capable of infusion and discharge of a specimen solution. An antibody immobilization layer 8 is formed on the bottom of the reaction hole 4. The surface of antibody immobilization layer 8 is masked with a masking composition comprising at least a buffer agent and a salt.

Such an optical waveguide type antibody chip is used in combination with a light receiving element, such as a laser oscillator, which directs light into the incident-side grating 2a, and a photoelectric conversion element, which receives light emitted from the emitting-side grating 2b.

The incident-side grating 2a and the emitting-side grating 2b are preferably formed by, for example, titanium oxide ($TiO_2$), tin oxide ($SnO_2$), zinc oxide, lithium niobate, gallium arsenide (GaAs), indium tin oxide (ITO), or polyimide.

The gratings 2a, 2b respectively have optical functions for introducing and emitting laser light into/from an optical waveguide type antibody chip. However, if similar functions can be achieved using another member, the gratings are not required. Additionally, if similar functions can be achieved, another optical element, such as a prism, may be used.

The optical waveguide layer can be arranged by separately forming a layer having a higher refraction index than that of a glass substrate on the surface of the substrate. This layer with a higher refraction index (optical waveguide layer) can be formed by, for example, ion-exchanging the glass components of the glass substrate with an element such as potassium or sodium.

The optical waveguide type antibody chip according to the embodiment performs an enzyme reaction within the reaction hole 4 and forms an enzyme reaction product exhibited color and to be precipitated, so that a specimen solution poured thereinto can be sufficiently measured if it is an amount of about 1 µL.

The water repellent resin layer 3 is placed so as to cover the region, excluding at least a part of the antibody immobilization layer 8 and the region in which the frame-shaped cell wall 5 is arranged, of the primary face constituting the entire reflection face of the substrate 1. A light shielding colored, e.g., black, resin is preferably used in the water repellent resin layer 3 so as to prevent the light entering from below the substrate 1 leaking out. A fluorine resin is particularly suitable for the water repellent resin.

Providing the cell wall 6 on the substrate 1 enables the prevention of chemical corrosion of the optical waveguide type antibody chip caused due to the presence of various chemicals used. The frame-shaped cell wall 6, as long as it has a structure that does not react with chemicals to be used, may be freely determined for convenience purposes in its size, height, shape of opening, material, etc. The material of the frame-shaped cell wall 6 is particularly preferably formed with a colored, e.g., black, resin. This colored resin material is not particularly limited so long as it does not have reactivity or compatibility with reagents, solvents, and the like, and has good formability. For example, acrylic resins, ABS resins, and the like can be used therefor.

The cell wall 6 is directly affixed with, for example, a UV curing adhesive so as to surround the reaction hole 4 opened in the primary face constituting the entire reflection face of the substrate 1 forming the optical waveguide layer. The frame-shaped cell wall 6 surrounds the reaction hole 4 such that a chemical solution such as a reagent/specimen solution or a cleaning solution introduced into the reaction hole 4 leaks outside. Hence, the height (thickness) from the substrate surface specified by the frame-shaped cell wall end is formed higher than the height of the water repellent resin film 3.

The antibody immobilization layer 8 has a structure in which, for example, a primary antibody is immobilized by means of a crosslinking polymer. The crosslinking polymer used in the antibody immobilization layer 8 introduces a functional group such as an amino group onto the surface of the substrate with a silane coupling agent and crosslinks the amino acid introduced into the substrate with an amino acid of an antibody with a crosslinking agent such as glutaraldehyde. In addition, the functional group utilized in crosslinking is not limited to an amino group.

Examples include a polymer containing a hydrogen bonding functional group, such as a photocrosslinking polyvinyl alcohol. Since an antibody is generally hydrophilic, an antibody immobilization layer also preferably has hydrophilicity.

The thickness of the antibody immobilization layer 8 (distance from the optical waveguide layer surface to the antibody immobilization layer surface) is desirably from 30 nm to 500 nm, more preferably 100 nm or less, most preferably 80 nm or less.

The antibody immobilization layer 8 is masked with a masking composition comprising at least a buffer agent and a salt on its surface. In a preferable embodiment, this masking includes a form of a film containing the masking composition in the surface of the antibody immobilization layer 8, or a form in which the masking composition are dispersed. A preferable combination of the masking composition can include, for example, TBS [Tris buffer+NaCl]. In particular, the masking composition comprising 100 mM Tris+100 mM NaCl of TBS is preferred since a crystal of NaCl is not generated, a well dispersed uniform surface state can be maintained, and storage durability can be maintained, after the TBS is coated on an antibody immobilization layer, dried and stored for 4 days in a nitrogen atmosphere.

Moreover, the masking composition further comprises at least one substance selected from proteins and surfactants. For example, bovine serum albumin (BSA) is preferred that it acts as a carrier protein to the TBS to improve the stability during storage. In addition, BSA can be expected to have an effect of preventing non-specific bonds during specimen reaction. Ionic, non-ionic and amphoteric surfactants in the surfactants can each be utilized, and examples thereof include surfactants commercially available as Tween 20, Tween 40, Tween 60 and Tween 80 (trade names, available from Atlas Powder Company). Of these additives, BSA and Tween 20 are preferred. Particularly preferable is an optical waveguide type antibody chip which has an antibody immobilization layer the surface of which is masked with a masking composition consisting of 100 mM Tris+100 mM NaCl+0.1% BSA+0.01% Tween 20. This is because, in the measurement of an antigen (e.g., insulin in plasma) in a specimen solution, this enables the highest correlation with measurement concentration values with use of the ELISA method.

Next, one example of a process of producing the optical waveguide type antibody chip according to the embodiment will be described with reference to FIGS. 3A to 3E.

As shown in FIG. 3A, for example, titanium oxide is sputter coated or spin coated on the surface of a substrate 1 composed of borosilicate glass to form a titanium oxide thin film 2.

Next, as shown in FIG. 3B, the titanium oxide thin film 2 is selectively etched and patterned by a photo-etching technique to form an incident-side grating 2a and an emitting-side grating 2b on the surfaces of both the ends of the substrate 1. This enables formation of an optical waveguide layer in the substrate 1 between gratings 2a, 2b of a thickness of about 1 μm.

Then, as shown in FIG. 3C, a water repellent resin, e.g., light shielding colored fluorine resin, is printed on the surface of the substrate 1, including the incident-side grating 2a and the emitting-side grating 2b, thereby forming a water repellent resin 3 having a circular reaction hole 4 and a rectangular frame-shaped trench 5, for example, surrounding the reaction hole 4 in a concentric circular fashion.

Next, as shown in FIG. 3D, a rectangular frame-shaped cell wall 6 made of, for example, a black ABS resin is inserted into the rectangular frame-shaped trench 5 of the water repellent resin 3. An ultraviolet ray curing adhesive interposed between the substrate (optical waveguide layer) 1 exposed to the trench 5 and the bottom of the cell wall 6 is cured by ultraviolet ray irradiation to cause the frame-shaped cell wall 6 to adhere to the surface of the substrate 1, thereby forming a cell 7 including the reaction hole 4.

As shown in FIG. 3E, an antibody immobilization layer 8 is then formed within the reaction hole 4.

The antibody immobilization layer 8 is specifically fabricated in the following technique.

(1) A surface portion of the substrate 1 exposed from the reaction hole 4 is subjected to a silane coupling treatment using aminopropyltrimethoxysilane of a silane coupling agent, thereby modifying the surface of the substrate 1 with an amino group.

(2) An antibody is immobilized on the substrate 1 exposed from the reaction hole 4 by crosslinking with glutaraldehyde.

(3) After implementation of cleaning and the like, the antibody immobilization layer 8 is formed on the surface of substrate 1 exposed from the reaction hole 4 by blocking with bovine serum albumin (BSA) or the like.

After the formation of the antibody immobilization layer 8, the surface of the antibody immobilization layer 8 is masked with (e.g., subjected to dropwise addition of) a solution containing a masking composition comprising at least a buffer agent and a salt, and dried to produce an optical waveguide type antibody chip.

Next, a method of measuring an antigen concentration according to the embodiment will be described using the above-described optical waveguide type antibody chip shown in FIGS. 1 and 2.

First, a specimen solution containing an antigen is added dropwise onto the antibody immobilization layer 8 within the cell 7 and subjected to antigen-antibody reaction to form a primary antigen-antibody complex. In other words, the antigen in the specimen solution is immobilized on the antibody immobilization layer 8. A secondary antibody marked with an enzyme is added dropwise onto the antibody immobilization layer to form a primary antibody-antigen-secondary antibody complex. Thereafter, a color reagent solution is added dropwise thereto to react with the enzyme of the secondary antibody to form an enzyme reactant exhibited color.

Next, before and after the dropwise addition of the color reagent solution, light (e.g., a laser beam) is made incident from the back face of the substrate 1 of the optical waveguide type antibody chip and into the optical waveguide layer of the substrate 1 from the incident-side grating 2a. The light emitted from the emitting-side grating 2b through the optical waveguide layer is received to measure the physical quantity of light, and then the concentration of the antigen in the above specimen solution is calculated on the basis of the measured physical quantity of light. In other words, the laser beam is totally reflected at the interface between the optical waveguide layer and the antibody immobilization layer 8 in the course of propagating through the optical waveguide layer to generate an evanescent wave. When the evanescent wave is totally reflected on the antibody immobilization layer 8 on which the enzyme reactant is present, it receives a physical quantity of light, for example, an attenuation action of light intensity, corresponding to the amount of the enzyme reactant by the interaction with this enzyme reactant. Evaluation is made for the intensity change in light (intensity difference in light) totally reflected when the enzyme reactant is not present prior to the dropwise addition of the color reagent solution and when the enzyme reactant is present after the dropwise addition of the color reagent solution. This light intensity difference is collated with a calibration curve prepared in advance, that is, a calibration curve having a relationship of the difference in the above light intensity obtained by measuring known antigen concentrations and a known antigen using the optical waveguide type antibody chip, to calculate the concentration of an antigen of a measuring target in the specimen solution. This enables measurement of the antigen concentration in the specimen solution.

The oxidation-reduction enzyme used in the marking enzyme is not particularly limited, and examples thereof include active enzymes such as peroxidase extracted from milk, horseradish, white blood cell, and catalase. Of these, peroxidase extracted from horseradish is particularly preferred.

A preferable aspect of the color reagent is that a color substrate is a benzidine color agent and a substrate of a marking enzyme is a peroxide. The benzidine color agents include, for example, 4-chloro-1-naphthol, 3,3'-diaminobenzidine, and 3,3',5,5'-tetramethylbenzidine. Of these, 3,3',5,5'-tetramethylbenzidine (hereinafter, referred to as TMBZ) or its hydrochloride (3,3',5,5'-tetramethylbenzidine.2HCl.2H$_2$O) is preferred from the viewpoint of measurement sensitivity. As the peroxide, for example, hydrogen peroxide can be used.

Next, the method of determining an antigen concentration using the above-described optical waveguide type antibody chip will be set forth specifically.

The antibody immobilization layer 8, on which a primary antibody for specifically recognizing an antigen (e.g., insulin) of a measuring target such as a protein and DNA has been immobilized, is formed on the surface of the substrate 1 within the reaction hole 4 of the optical waveguide type antibody chip. When, for example, 1.0 to 5 µL of a specimen solution containing an antigen is added dropwise onto the antibody immobilization layer 8 within the reaction hole 4, the antigen is linked to the primary antibody to form an immune complex of a primary antibody/antigen.

Next, cleaning is performed using a cleaning liquid, such as a Tris buffer solution (TBS) having added thereto a surfactant in order to enhance the cleaning effect of the specimen solution other than the antigen linked to the primary antibody.

A secondary antibody solution marked with an enzyme is then added dropwise. When the secondary antibody solution marked with the enzyme is added dropwise, the secondary antibody is further linked to the antigen at a site other than the site of the primary antibody. As a result, an immune complex including a primary antibody/antigen/secondary antibody is formed. In addition, as a marking enzyme marked on the secondary antibody, for example, peroxidase or the like can be used as an oxidation-reduction enzyme.

Next, the secondary antibody solution containing the secondary antibody having not formed an immune complex is cleaned again using a cleaning solution such as the above TBS suffer solution.

Then, the above TBS buffer solution used for cleaning is removed and a phosphate buffer solution is poured for the purpose of stabilization.

Subsequently, a laser beam or the like is irradiated from a luminous element toward the incident-side grating 2a of the optical waveguide type antibody chip to propagate through the optical waveguide layer. At this time, an evanescent wave is emitted from the surface of the optical waveguide layer. This propagated light is received with a light receiving element as reflection light from the emitting-side grating 2b and measured as a reference reflection light intensity.

Next, a color reagent solution is added dropwise to the cell 7 containing the antibody immobilization layer 8 of the antibody chip. As the color reagent solution, a solution is preferably used that is prepared by containing acetic acid, TMBZ, hydrogen peroxide (H$_2$O$_2$) and a small amount of an organic solvent such as dimethylsulfoxide in a buffer solution of a pH of 4.9. The drowise addition of the color reagent solution leads to an oxidation-reduction enzyme reaction between the marking enzyme such as peroxidase (POD) and the H$_2$O$_2$ of the substrate of the marking enzyme (POD) to form a radical oxygen atom (O*). The radical oxygen atom (O*) formed by the enzyme reaction oxidizes the color reagent, for example, the NH$_2$ group of TMBZ is oxidized to the =NH group, which exhibits blue green color and is further insolubilized and precipitated within the antibody immobilization layer 8 (the surface of the substrate 1).

A laser beam is then made incident into the substrate 1 of the optical waveguide type antibody chip, as in the measurement of the reference reflection light intensity. In other words, when a laser beam or the like is irradiated from a luminous element toward the incident-side grating 2a of the optical waveguide type antibody chip, the incident laser beam propagates in a total-reflection fashion through the substrate 1 of the optical waveguide layer via the incident-side grating 2a. When the laser beam is totally reflected, an evanescent wave is generated on the optical waveguide layer surface. This evanescent wave is absorbed by the precipitated enzyme reactant. On the basis of this action, the light propagating through the optical waveguide layer receives a very small change, which thus attenuates the light. The reflection light from the emitting-side grating 2b is received by a light receiving element and the reflection light intensity after exhibiting color is measured.

Next, the difference in light intensity between the reference reflection light intensity already determined and the reflection light intensity after exhibiting color is collated with a calibration curve prepared in advance, whereby it is possible to calculate the concentration of the antigen (e.g., insulin, proteins) in the specimen solution. A calibration curve is prepared by plotting the relation of the differences in light intensity between the reference reflection light intensity obtained by measuring a known antigen concentration and a specimen solution having a known antigen concentration using an optical waveguide type antibody chip and the reflection light intensity after exhibiting color.

In the measurement of an antigen concentration, impurities (e.g., lipids in plasma) in a specimen solution act as substances that inhibit an antigen-antibody reaction between an antibody of the antibody immobilization layer and an antigen in the specimen solution. For this reason, the difference in light intensity between the reference reflection light intensity and the reflection light intensity after exhibiting color is small as compared with the case where the antigen-antibody reaction is not inhibited. As a result, the concentration of the antigen obtained by collation with the calibration curve is calculated as a small value compared with the actual antigen concentration in the specimen solution. In addition, the lowered degree of this antigen concentration is also deviated due to influence of impurities in the specimen solution.

Thus, a masking composition comprising at least a buffer agent and a salt is masked on the surface of the antibody immobilization layer of the optical waveguide type antibody chip according to the embodiment. For example, a film containing the masking composition is formed on the surface of the antibody immobilization layer. This makes it possible to suppress the influence of substances inhibiting an antigen-antibody reaction between an antibody of the antibody immobilization layer and an antigen in the specimen solution. As a consequence, in the concentration measurement, the antigen concentration obtained by collating the difference in light intensity between the reference reflection light intensity and the reflection light intensity after exhibiting color with a calibration curve prepared in advance can be calculated as a value approximated to the actual antigen concentration in the specimen solution. That is, an antigen concentration in a specimen solution can be measured with high precision and, for example, an antigen concentration in a specimen solution can be measured with a high correlation with a concentration value obtained by measuring an antigen concentration in a specimen solution by the ELISA method.

The above specimen solution can utilize any of, for example, whole blood, serum, and plasma. The optical waveguide type antibody chip according to the embodiment carries out the primary, secondary and enzyme reactions on the antibody immobilization layer within the reaction hole located in a portion of the optical waveguide layer in the substrate surface and then detects information of the antibody immobilization layer by making use of an evanescent wave propagating through the optical waveguide layer. Therefore, the amount of a specimen solution applied to measurement may be a certain amount or more, and the concentration of an antigen such as insulin can be measured even if the amount of a specimen solution for measurement is imprecise.

In addition, the method of determining an antigen concentration of the embodiment not only measures the amount of transmitted light of a well using a microplate, as in the conventional method, but also observes the light intensity change of reflection light attributable to absorption of an evanescent wave generated during its total reflection on the antibody immobilization layer, so that the area needed for measurement can be decreased. As a result, even with a specimen solution of 5 µL or less, normally from 1.0 to 5 µL, in a suitable condition, from 1.0 to 2 µL, the antigen concentration can be measured.

In the intensity measurement of light totally reflected, generally zero-th light totally reflected is used, but the measurement is not limited thereto. Observation may be done by means of diffraction light, that is, high-order light totally reflected, such as primary or secondary light, or other appropriate phenomena/methods.

The examples of the present invention will be described hereinafter.

Example 1

The insulin concentration of a rat was measured using the optical waveguide type antibody chip shown in FIGS. 1 and 2, described in the method of the above-described embodiment. An anti-insulin antibody was immobilized on the antibody immobilization layer 8 (within the range of a circle of a diameter of 2 mm) within the reaction hole 4 on the optical waveguide layer of the substrate 1. Moreover, onto the antibody immobilization layer 8, a masking composition solution of 1.5 µm of 100 mM Tris+100 mM NaCl+0.1% BSA+0.01% Tween 20 (trade name, Atlas Powder Company) was added dropwise and dried.

<Preparation of Calibration Curve>

1.5 µL of insulin solutions of a rat (standard) with concentrations of 3.2 ng/mL and 6.4 ng/mL were prepared as specimen solutions. These rat insulin solutions of 1.5 µL were added dropwise onto the antibody immobilization layer 8 within the cell 7 of the optical waveguide type antibody chip, and a primary reaction was made at 37° C. for 10 minutes, followed by cleaning with a TBS buffer solution (containing 0.1% Tween 20). A secondary antibody solution enzyme-marked with peroxidase extracted from horseradish was added dropwise thereto and a secondary reaction was made at 37° C. for 10 minutes. After the secondary reaction, the reactant solution was cleaned with the TBS buffer solution and further with a buffer solution.

Subsequently, a laser beam was irradiated from a luminous element toward the incident-side grating 2a of the optical waveguide type antibody chip to propagate through the optical waveguide layer. At this time, the laser beam was totally reflected at the back face of the antibody immobilization layer 8. The reflected light was emitted outside the substrate 1 by the emitting-side grating 2b, received by a light receiving element (photodiode), and measured as a reference reflection light intensity. The intensity of the light flux after total reflection changes according to the absorption and reflection of an evanescent wave made incident onto the sensing area of the antibody immobilization layer 8 during total reflection.

Next, after the measurement of the reference reflection light intensity, a color reagent solution (3,3',5,5'-tetramethylbenzidine 1.1 mmol/L, hydrogen peroxide 1.9 mmol/L, dimethylsulfoxide 1 volume %, an acetic acid buffer solution 80 mmol/L, pH 4.9) was added dropwise into the reaction hole 4 within the cell 7. Over 10 minutes immediately after the addition, a laser beam was irradiated from the luminous element toward the incident-side grating 2a of the optical waveguide type antibody chip to propagate through the optical waveguide layer. At this time, the laser beam was totally reflected at the back face of the antibody immobilization layer 8. The reflected light was emitted outside the substrate 1 by the emitting-side grating 2b, received by the light receiving element (photodiode), and measured as a reflection light intensity after exhibiting color. More specifically, over 10 minutes immediately after the dropwise addition of the color reagent solution, a change in the reflection light intensity after exhibiting color was measured.

The differences in reference reflection intensities and reflection light intensities after exhibiting color measured in such operation were evaluated, and these reflection light intensity differences and the insulin concentrations of 3.2 ng/mL and 6.4 ng/mL were plotted to prepare a calibration curve (abscissa: reflection light intensity difference, ordinate: insulin concentration).

<Actual Measurement of Insulin of Rats>

1.5 μL of insulin solutions of four different rats (Zucker#1) with different dilution magnifications were prepared. For the insulin solutions of these rats (Zucker#1), reference reflection light intensities and reflection light intensities after exhibiting color were measured through the same operation as in the preparation of the above calibration curve. Further, the differences of the reference reflection light intensities and reflection light intensities after exhibiting color were obtained. These reflection intensity differences were collated with the calibration curve prepared in the above-mentioned method to calculate the insulin concentrations of the rats (Zucker#1).

The relationship between the measurement value of the calculated insulin concentration of each rat (Zucker#1) and the measurement value of the insulin concentration of each rat (Zucker#1) by means of the ELISA method is shown in FIG. 4.

Example 2

1.5 μL of insulin solutions of a rat (standard) with concentrations of 3.2 ng/mL and 6.4 ng/mL were prepared as specimen solutions. The differences in reference reflection intensities and reflection light intensities after exhibiting color and the insulin concentrations of 3.2 ng/mL and 6.4 ng/mL of the rat were plotted to prepare a calibration curve (abscissa: reflection light intensity difference, ordinate: insulin concentration) by means of the same method as in Example 1, and using an optical waveguide type antibody chip having the same configuration as in Example 1.

1.5 μL of insulin solutions of four different rats (Zucker#2) with different dilution magnifications were prepared. For the insulin solutions of these rats (Zucker#2), reference reflection light intensities and reflection light intensities after exhibiting color were measured through the same operation as in the preparation of the above calibration curve. Further, the differences in the reference reflection light intensities and reflection light intensities after exhibiting color were obtained. These reflection intensity differences were collated with the above calibration curve to calculate the insulin concentrations of the rats (Zucker#2).

The relationship between the measurement value of the calculated insulin concentration of each rat (Zucker#2) and the measurement value of the insulin concentration of each rat (Zucker#2) by means of the ELISA method is shown in FIG. 4.

Example 3

1.5 μL of insulin solutions of a rat (standard) with concentrations of 3.2 ng/mL and 6.4 ng/mL were prepared as specimen solutions. The differences in reference reflection intensities and reflection light intensities after exhibiting color and the insulin concentrations of 3.2 ng/mL and 6.4 ng/mL of the rat were plotted to prepare a calibration curve (abscissa: reflection light intensity difference, ordinate: insulin concentration) by means of the same method as in Example 1, and using an optical waveguide type antibody chip having the same configuration as in Example 1.

1.5 μL of insulin solutions of four different rats (db/db#3) with different dilution magnifications were prepared. For the insulin solutions of these rats (db/db#3), reference reflection light intensities and reflection light intensities after exhibiting color were measured through the same operation as in the preparation of the above calibration curve. Further, the differences in the reference reflection light intensities and reflection light intensities after exhibiting color were obtained. These reflection intensity differences were collated with the above calibration curve to calculate the insulin concentrations of the rats (db/db#3).

The relationship between the measurement value of the calculated insulin concentration of each rat (db/db#3) and the measurement value of the insulin concentration of each rat (db/db#3) by means of the ELISA method is shown in FIG. 4.

Example 4

1.5 μL of insulin solutions of a rat (standard) with concentrations of 3.2 ng/mL and 6.4 ng/mL were prepared as specimen solutions. The differences in reference reflection intensities and reflection light intensities after exhibiting color and the insulin concentrations of 3.2 ng/mL and 6.4 ng/mL of the rat were plotted to prepare a calibration curve (abscissa: reflection light intensity difference, ordinate: insulin concentration) by means of the same method as in Example 1, and using an optical waveguide type antibody chip having the same configuration as in Example 1.

1.5 μL of insulin solutions of four different rats (db/db#5) with different dilution magnifications were prepared. For the insulin solutions of these rats (db/db#5), reference reflection light intensities and reflection light intensities after exhibiting color were measured through the same operation as in the preparation of the above calibration curve. Further, the differences in the reference reflection light intensities and reflection light intensities after exhibiting color were obtained. These reflection intensity differences were collated with the above calibration curve to calculate the insulin concentrations of the rats (db/db #5).

The relationship between the measurement value of the calculated insulin concentration of each rat (db/db#5) and the measurement value of the insulin concentration of each rat (db/db#5) by means of the ELISA method is shown in FIG. 4.

Comparative Example 1

The insulin concentration of a rat was measured using an optical waveguide type antibody chip configured such that an anti-insulin antibody was immobilized on an antibody immobilization layer (within the range of a circle of a diameter of 2 mm) within a reaction hole on an optical waveguide layer of a substrate. More specifically, used was an optical waveguide type antibody chip having the same structure as in FIGS. 1 and 2 described above except for including an antibody immobilization layer without treatment of dropwise adding of a solution of 100 mM Tris+100 mM NaCl+0.1% BSA+0.01% Tween 20 (trade name, Atlas Powder Company) and drying as in Examples 1 to 4.

<Forming the Calibration Curve>

1.5 μL of insulin solutions of a rat (standard) with concentrations of 3.2 ng/mL and 6.4 ng/mL were prepared as specimen solutions. These rat insulin solutions of 1.5 µL were added dropwise onto an antibody immobilization layer within a cell of an optical waveguide type antibody chip, and a primary reaction was made at 37° C. for 10 minutes, followed by cleaning with a TBS buffer solution (containing 0.1% Tween 20). A secondary antibody solution enzyme-marked with horseradish peroxidase was added dropwise thereto and a secondary reaction was made at 37° C. for 10 minutes. After the secondary reaction, the reactant solution was cleaned with the above TBS buffer solution and further with a buffer solution.

Next, a laser beam was irradiated from a luminous element toward an incident-side grating of the optical waveguide type antibody chip to propagate through the optical waveguide layer. At this time, the laser beam was totally reflected at the back face of the antibody immobilization layer. The reflected light was emitted outside the substrate by an emitting-side grating, received by a light receiving element (photodiode), and measured as a reference reflection light intensity. The intensity of the light flux after total reflection changes according to the absorption and reflection of an evanescent wave made incident onto the sensing area of the antibody immobilization layer during total reflection.

After the measurement of the reference reflection light intensity, a color reagent solution (tetramethylbenzidine 1.1 mmol/L, hydrogen peroxide 1.9 mmol/L, dimethylsulfoxide 1 volume %, and an acetic acid buffer solution 80 mmol/L, pH 4.9) was added dropwise into the reaction hole within the cell. Over 10 minutes immediately after the addition, a laser beam was irradiated from the luminous element toward the incident-side grating of the optical waveguide type antibody chip to propagate through the optical waveguide layer. At this time, the laser beam was totally reflected at the back face of the antibody immobilization layer. The reflected light was emitted outside the substrate by the emitting-side grating, received by the light receiving element (photodiode), and measured as a reflection light intensity after exhibiting color. In other words, over 10 minutes immediately after the dropwise addition of the color reagent solution, a change in the reflection light intensity after exhibiting color was measured.

The differences of reference reflection intensities and reflection light intensities after exhibiting color measured in such operation were evaluated, and these reflection light intensity differences and the insulin concentrations of 3.2 ng/mL and 6.4 ng/mL were plotted to prepare a calibration curve (abscissa: reflection light intensity difference, ordinate: insulin concentration).

<Actual Measurement of Insulin of Rats>

1.5 µL of insulin solutions of four different rats (Zucker#1) with different dilution magnifications were prepared. For the insulin solutions of these rats (Zucker#1), reference reflection light intensities and reflection light intensities after exhibiting color were measured through the same operation as in the preparation of the above calibration curve. Further, the differences in the reference reflection light intensities and reflection light intensities after exhibiting color were obtained. These reflection intensity differences were collated with the calibration curve prepared in the above-mentioned method to calculate the insulin concentrations of the rats (Zucker#1).

The relationship between the measurement value of the calculated insulin concentration of each rat (Zucker#1) and the measurement value of the insulin concentration of each rat (Zucker#1) by means of the ELISA method is shown in FIG. 5.

Comparative Example 2

1.5 µL of insulin solutions of a rat (standard) with concentrations of 3.2 ng/mL and 6.4 ng/mL were prepared as specimen solutions. The differences in reference reflection intensities and reflection light intensities after exhibiting color and the insulin concentrations of 3.2 ng/mL and 6.4 ng/mL of the rat were plotted to prepare a calibration curve (abscissa: reflection light intensity difference, ordinate: insulin concentration) by means of the same method as in Example 1, and using an optical waveguide type antibody chip having the same configuration as in Comparative Example 1.

1.5 µL of insulin solutions of four different rats (Zucker#2) with different dilution magnifications were prepared. For the insulin solutions of these rats (Zucker#2), reference reflection light intensities and reflection light intensities after exhibiting color were measured through the same operation as in the preparation of the above calibration curve. Further, the differences in the reference reflection light intensities and reflection light intensities after exhibiting color were obtained. These reflection intensity differences were collated with the above calibration curve to calculate the insulin concentrations of the rats (Zucker#2).

The relationship between the measurement value of the calculated insulin concentration of each rat (Zucker#2) and the measurement value of the insulin concentration of each rat (Zucker#2) by means of the ELISA method is shown in FIG. 5.

Comparative Example 3

1.5 µL of insulin solutions of a rat (standard) with concentrations of 3.2 ng/mL and 6.4 ng/mL were prepared as specimen solutions. The differences in reference reflection intensities and reflection light intensities after exhibiting color and the insulin concentrations of 3.2 ng/mL and 6.4 ng/mL of the rat were plotted to prepare a calibration curve (abscissa: reflection light intensity difference, ordinate: insulin concentration) by means of the same method as in Comparative Example 1, and using an optical waveguide type antibody chip having the same configuration as in Comparative Example 1.

1.5 µL of insulin solutions of four different rats (db/db#3) with different dilution magnifications were prepared. For the insulin solutions of these rats (db/db#3), reference reflection light intensities and reflection light intensities after exhibiting color were measured through the same operation as in the preparation of the above calibration curve. Further, the differences in the reference reflection light intensities and reflection light intensities after exhibiting color were obtained. These reflection intensity differences were collated with the above calibration curve to calculate the insulin concentrations of the rats (db/db#3).

The relationship between the measurement value of the calculated insulin concentration of each rat (db/db#3) and the measurement value of the insulin concentration of each rat (db/db#3) by means of the ELISA method is shown in FIG. 5.

Comparative Example 4

1.5 µL of insulin solutions of a rat (standard) with concentrations of 3.2 ng/mL and 6.4 ng/mL were prepared as specimen solutions. The differences in reference reflection intensities and reflection light intensities after exhibiting color and the insulin concentrations of 3.2 ng/mL and 6.4 ng/mL of the rat were plotted to prepare a calibration curve (abscissa: reflection light intensity difference, ordinate: insulin concentration) by means of the same method as in Comparative Example 1, and using an optical waveguide type antibody chip having the same configuration as in Comparative Example 1.

1.5 µL of insulin solutions of four different rats (db/db#5) with different dilution magnifications were prepared. For the insulin solutions of these rats (db/db#5), reference reflection light intensities and reflection light intensities after exhibiting color were measured through the same operation as in the preparation of the above calibration curve. Further, the differences in the reference reflection light intensities and reflection light intensities after exhibiting color were obtained. These reflection intensity differences were collated with the above calibration curve to calculate the insulin concentrations of the rats (db/db#5).

The relationship between the measurement value of the calculated insulin concentration of each rat (db/db#5) and the measurement value of the insulin concentration of each rat (db/db#5) by means of the ELISA method is shown in FIG. 5.

As clear from FIG. 4, the relation of the measurements (y) of the insulin concentrations of various rats and mice calculated in Examples 1 to 4 and the measurements (x) of the insulin concentrations of various rats and mice by means of the ELISA method is represented by a linear function of y=1.0682x and the correlation coefficient ($R^2$) is 0.9616. This indicates a very high correlation with the measurements of the insulin concentrations of various rats and mice by means of the ELISA method, so that highly precise the measurement of insulin concentrations is possible.

On the contrary, as clear from FIG. 5, the relation of the measurements (y) of the insulin concentrations of various rats and mice calculated in Comparative Examples 1 to 4 and the measurements (x) of the insulin concentrations of various rats and mice by means of the ELISA method is represented by a linear function of y=0.4784x and the correlation coefficient ($R^2$) is 0.684. This indicates a low correlation with the measurements of the insulin concentrations of various rats and mice by means of the ELISA method, whereby the precision of insulin concentration measurement is low.

Example 5

1.5 µL of insulin solutions of a mouse (standard) with concentrations of 3.2 ng/mL and 6.4 ng/mL were prepared as specimen solutions. The differences in reference reflection intensities and reflection light intensities after exhibiting color and the insulin concentrations of 3.2 ng/mL and 6.4 ng/mL of the mouse were plotted to prepare a calibration curve (abscissa: reflection light intensity difference, ordinate: insulin concentration) by means of the same method as in Example 1, and using an optical waveguide type antibody chip having the same configuration as in Example 1.

1.5 µL of insulin solutions of mice (db/db#A) with different dilution magnifications were prepared. For the insulin solutions of these mice (db/db#A), reference reflection light intensities and reflection light intensities after exhibiting color were measured through the same operation as in the preparation of the above calibration curve. Further, the differences in the reference reflection light intensities and reflection light intensities after exhibiting color were obtained. These reflection intensity differences were collated with the above calibration curve to calculate the insulin concentrations of the mice (db/db#A).

Figure 6:
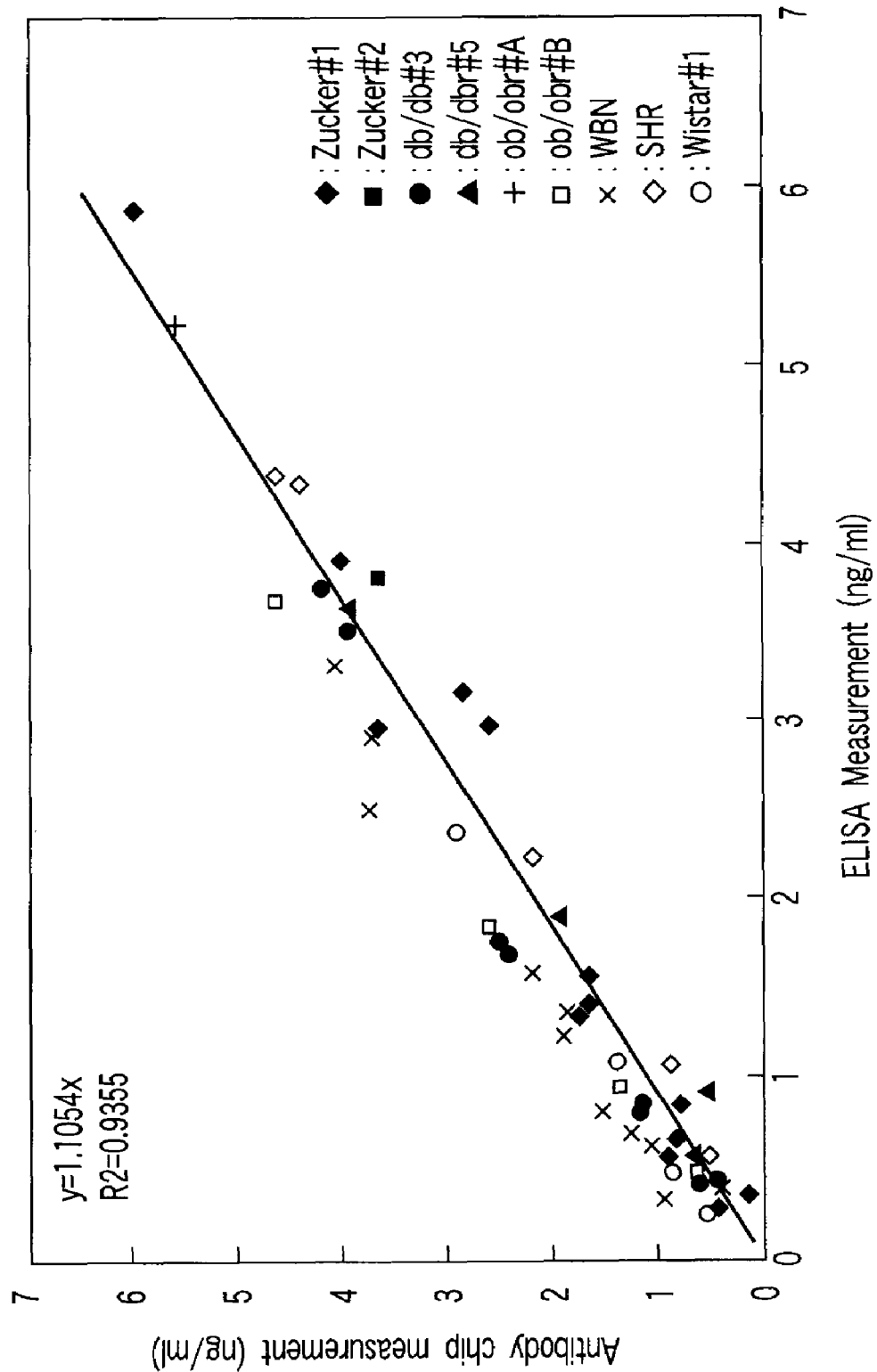
FIG. 6 is a graph showing a relation between measurements (y) of insulin concentrations of various rats and mice, calculated from Examples 1 to 9, and measurements (x) of insulin concentrations of various rats and mice, calculated by the ELISA method.

The relationship between the measurement value of the calculated insulin concentration of each mouse (db/db#A) and the measurement value of the insulin concentration of each mouse (db/db#A) by means of the ELISA method is shown in FIG. 6.

Example 6

1.5 µL of insulin solutions of a mouse (standard) of concentrations of 3.2 ng/mL and 6.4 ng/mL were prepared as specimen solutions. The differences in reference reflection intensities and reflection light intensities after exhibiting color and the insulin concentrations of 3.2 ng/mL and 6.4 ng/mL of the mouse were plotted to prepare a calibration curve (abscissa: reflection light intensity difference, ordinate: insulin concentration) by means of the same method as in Example 1, and using an optical waveguide type antibody chip having the same configuration as in Example 1.

1.5 µL of insulin solutions of mice (db/db#B) of different dilution magnifications were prepared. For the insulin solutions of these mice (db/db#B), reference reflection light intensities and reflection light intensities after exhibiting color were measured through the same operation as in the preparation of the above calibration curve. Further, the differences in the reference reflection light intensities and reflection light intensities after exhibiting color were obtained. These reflection intensity differences were collated with the above calibration curve to calculate the insulin concentrations of the mice (db/db#B).

The relationship between the measurement value of the calculated insulin concentration of each mouse (db/db#B) and the measurement value of the insulin concentration of each mouse (db/db#B) by means of the ELISA method is shown in FIG. 6.

Example 7

1.5 µL of insulin solutions of a rat (standard) with concentrations of 3.2 ng/mL and 6.4 ng/mL were prepared as specimen solutions. The differences in reference reflection intensities and reflection light intensities after exhibiting color and the insulin concentrations of 3.2 ng/mL and 6.4 ng/mL of the rat were plotted to prepare a calibration curve (abscissa: reflection light intensity difference, ordinate: insulin concentration) by means of the same method as in Example 1, and using an optical waveguide type antibody chip having the same configuration as in Example 1.

1.5 µL of insulin solutions of rats (WBN) of different dilution magnifications were prepared. For the insulin solutions of these rats (WBN), reference reflection light intensities and reflection light intensities after exhibiting color were measured through the same operation as in the preparation of the above calibration curve. Further, the differences in the reference reflection light intensities and reflection light intensities after exhibiting color were obtained. These reflection intensity differences were collated with the above calibration curve to calculate the insulin concentrations of the rats (WBN).

The relationship between the measurement value of the calculated insulin concentration of each rat (WBN) and the measurement value of the insulin concentration of each rat (WBN) by means of the ELISA method is shown in FIG. 6.

Example 8

1.5 µL of insulin solutions of a rat (standard) with concentrations of 3.2 ng/mL and 6.4 ng/mL were prepared as specimen solutions. The differences in reference reflection intensities and reflection light intensities after exhibiting color and the insulin concentrations of 3.2 ng/mL and 6.4 ng/mL of the rat were plotted to prepare a calibration curve (abscissa: reflection light intensity difference, ordinate: insulin concentration) by means of the same method as in Example 1, and using an optical waveguide type antibody chip having the same configuration as in Example 1.

1.5 μL of insulin solutions of rats (SHR) of different dilution magnifications were prepared. For the insulin solutions of these rats (SHR), reference reflection light intensities and reflection light intensities after exhibiting color were measured through the same operation as in the preparation of the above calibration curve. Further, the differences in the reference reflection light intensities and reflection light intensities after exhibiting color were obtained. These reflection intensity differences were collated with the above calibration curve to calculate the insulin concentrations of the rats (SHR).

The relationship between the measurement value of the calculated insulin concentration of each rat (SHR) and the measurement value of the insulin concentration of each rat (SHR) by means of the ELISA method is shown in FIG. 6.

Example 9

1.5 μL of insulin solutions of a rat (standard) with concentrations of 3.2 ng/mL and 6.4 ng/mL were prepared as specimen solutions. The differences in reference reflection intensities and reflection light intensities after exhibiting color and the insulin concentrations of 3.2 ng/mL and 6.4 ng/mL of the rat were plotted to prepare a calibration curve (abscissa: reflection light intensity difference, ordinate: insulin concentration) by means of the same method as in Example 1, and using an optical waveguide type antibody chip having the same configuration as in Example 1.

1.5 μL of insulin solutions of rats (Wistar#1) with different dilution magnifications were prepared. For the insulin solutions of these rats (Wistar#1), reference reflection light intensities and reflection light intensities after exhibiting color were measured through the same operation as in the preparation of the above calibration curve. Further, the differences in the reference reflection light intensities and reflection light intensities after exhibiting color were obtained. These reflection intensity differences were collated with the above calibration curve to calculate the insulin concentrations of the rats (Wistar#1).

The relationship between the measurement value of the calculated insulin concentration of each rat (Wistar#1) and the measurement value of the insulin concentration of each rat (Wistar#1) by means of the ELISA method is shown in FIG. 6.

FIG. 6 also depicts the relation of the measurements of the insulin concentrations of various rats (Zucker#1, Zucker#2) and various mice (db/db#3 and db/db#5) calculated in Examples 1 to 4 described above and the measurements of the insulin concentrations of various rats (Zucker#1, Zucker#2) and various mice (db/db#3 and db/db#5) by means of the ELISA method.

As clear from FIG. 6, the relation of the measurements (y) of the insulin concentrations of various rats and mice calculated in Examples 1 to 9 and the measurements (x) of the insulin concentrations of various rats and mice by means of the ELISA method is represented by a linear function of $y=1.1054x$ and the correlation ($R^2$) is 0.9355. This indicates a very high correlation with the measurements of the insulin concentrations of various rats and mice by means of the ELISA method, so that highly precise measurement of insulin concentrations is possible.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical waveguide type antibody chip, comprising:
   a transparent substrate;
   an incident-side optical element and an emitting-side optical element placed at a distance from each other on a primary face of the substrate;
   a water repellent resin film formed on the primary face of the substrate including an optical waveguide layer formed between the optical elements, the water repellent resin film comprising a reaction hole having exposed the optical waveguide layer on its bottom and a frame-shaped trench surrounding the reaction hole;
   a rectangular frame-shaped cell wall which is fixed in the trench of the water repellent resin film and which forms a cell capable of infusion and discharge of a specimen solution together with the reaction hole; and
   an antibody immobilization layer formed on the bottom of the reaction hole, the surface of the antibody immobilization layer being masked with a masking composition comprising at least a buffer agent and a salt.

2. The optical waveguide type antibody chip according to claim 1, wherein the optical element is a grating.

3. The optical waveguide type antibody chip according to claim 1, wherein the water repellent resin film is a black fluorine resin film.

4. The optical waveguide type antibody chip according to claim 1, wherein the cell wall is made of a black acrylic resin or a black ABS resin.

5. The optical waveguide type antibody chip according to claim 1, wherein the buffer agent and the salt are a Tris buffer and sodium chloride, respectively.

6. The optical waveguide type antibody chip according to claim 1, wherein the masking composition further comprises at least one substance selected from proteins and surfactants.

7. The optical waveguide type antibody chip according to claim 6, wherein the protein is bovine serum albumin.

8. A method of measuring an antigen concentration, comprising:
   providing an optical waveguide type antibody chip comprising:
   (a) a transparent substrate;
   (b) an incident-side optical element and an emitting-side optical element placed at a distance from each other on a primary face of the substrate;
   (c) a water repellent resin film formed on the primary face of the substrate including an optical waveguide layer formed between the optical elements, the water repellent resin film comprising a reaction hole having exposed the optical waveguide layer on its bottom and a frame-shaped trench surrounding the reaction hole;
   (d) a rectangular frame-shaped cell wall which is fixed in the trench of the water repellent resin film and which forms a cell capable of infusion and discharge of a specimen solution together with the reaction hole; and
   (e) an antibody immobilization layer formed on the bottom of the reaction hole, the surface of the antibody immobilization layer being masked with a masking composition comprising at least a buffer agent and a salt;

adding dropwise a specimen solution containing an antigen onto the antibody immobilization layer within the cell to form a primary antibody-antigen complex;

adding dropwise a secondary antibody marked with an enzyme onto the antibody immobilization layer to form a primary antibody-antigen-secondary antibody complex;

adding dropwise a color reagent onto the antibody immobilization layer to allow the color reagent to react with the enzyme of the secondary antibody, thereby forming an enzyme reactant exhibited color;

causing light to be incident on an optical waveguide layer of the substrate from the incident-side optical element with respect to the substrate before and after the dropwise addition of the color reagent;

receiving the light emitted from the emitting-side optical element through the optical waveguide layer to measure light intensities before and after the dropwise addition of the color reagent; and calculating the antigen concentration in the specimen solution on the basis of the difference in the light intensities.

9. The method according to claim 8, wherein the specimen solution is any of whole blood, serum and plasma.

10. The method according to claim 8, wherein the forming antibody immobilization layer having the surface of which is masked with the masking composition comprises steps of:

immobilizing a primary antibody onto the bottom of the reaction hole of the substrate to form an antibody immobilization layer;

treating the surface of the antibody immobilization layer with a solution containing the masking composition; and drying the surface of the antibody immobilization layer.

11. The method according to claim 8, wherein the intensity of light emitted from the emitting-side optical element through the optical waveguide layer after dropwise addition of the color agent is decreased due to the fact that an evanescent wave generated when the light is totally reflected at an interface between the optical waveguide layer and the antibody immobilization layer is absorbed the enzyme reactant generated in the antibody immobilization layer and exhibited color.

12. The method according to claim 8, wherein the antigen concentration in the specimen solution is calculated by collating the difference in the light intensities with a calibration curve having a relation of the difference in the light intensities obtained by measuring a known antigen concentration and a specimen solution having a known antigen concentration using the optical waveguide type antibody chip before and after the dropwise addition of the color reagent.

* * * * *